US005619581A

United States Patent [19]

Ferguson et al.

[11] Patent Number: 5,619,581

[45] Date of Patent: Apr. 8, 1997

[54] ACTIVE NOISE AND VIBRATION CANCELLATION SYSTEM

[75] Inventors: Matthew K. Ferguson, Erie, Pa.; Steve C. Southward; Michael C. Heath, both of Cary, N.C.

[73] Assignee: Lord Corporation, Erie, Pa.

[21] Appl. No.: 245,717

[22] Filed: May 18, 1994

[51] Int. Cl.$^6$ .................... A61F 11/06; H03B 29/00

[52] U.S. Cl. .................... 381/71; 381/94

[58] Field of Search .................... 381/71, 72, 94

[56] References Cited

U.S. PATENT DOCUMENTS

| | | |
|---|---|---|
| 3,588,752 | 6/1971 | Hirshfield . |
| 3,626,315 | 12/1971 | Stirling et al. . |
| 3,635,427 | 1/1972 | Balke . |
| 3,690,607 | 9/1972 | Mard . |
| 3,694,776 | 9/1972 | Linder . |
| 3,810,038 | 5/1974 | Hershberg et al. . |
| 3,854,102 | 12/1974 | Seipel et al. . |
| 3,867,712 | 2/1975 | Harthill et al. . |
| 4,122,303 | 10/1978 | Chaplin et al. . |
| 4,153,815 | 5/1979 | Chaplin et al. . |
| 4,232,381 | 11/1980 | Rennick et al. . |
| 4,328,483 | 5/1982 | Swartz et al. . |
| 4,417,098 | 11/1983 | Chaplin et al. . |
| 4,453,143 | 6/1984 | Bennett . |
| 4,473,906 | 9/1984 | Warnaka et al. . |
| 4,519,084 | 5/1985 | Langseth . |
| 4,562,589 | 12/1985 | Warnka et al. . |
| 4,626,754 | 12/1986 | Habermann et al. . |
| 4,677,676 | 6/1987 | Eriksson . |
| 4,689,821 | 8/1987 | Salikuddin et al. . |
| 4,825,396 | 4/1989 | Gazsi . |
| 4,866,779 | 9/1989 | Kennedy et al. . |
| 4,872,127 | 10/1989 | Nolan . |
| 4,878,188 | 10/1989 | Ziegler, Jr. . |
| 4,922,530 | 5/1990 | Kenney et al. . |
| 5,000,415 | 3/1991 | Sandercock . |
| 5,038,269 | 8/1991 | Grimble et al. . |
| 5,057,993 | 10/1991 | Kanda . |
| 5,133,527 | 7/1992 | Chen et al. . |
| 5,142,240 | 8/1992 | Isota et al. . |
| 5,170,433 | 12/1992 | Elliott et al. . |
| 5,179,516 | 1/1993 | Choshitani et al. . |

OTHER PUBLICATIONS

PCT Patent Appl. No.PCT/US92?07802 having IPN WO 94/07212 published Mar. 31, 1994 entitled Sampled-Data Filter with Low Delay, assigned to Noise Cancellation Technologies.

*Theory and Design of Adaptive Filters,* Treichler et al., John Wiley & Sons, pp. 187–225.

*Primary Examiner*—Curtis Kuntz
*Assistant Examiner*—Minsun Oh
*Attorney, Agent, or Firm*—Richard K. Thomson; Randall S. Wayland; James W. Wright

[57] ABSTRACT

An active noise and vibration control system (20) for cancellation of noise or vibration. The system (20) provides a system whereby the adaptation path and feedforward path are implemented in separate hardware. As a result, the computational burden on the digital signal processor (DSP) (28) is reduced allowing the DSP (28) to handle multiple inputs (22), error sensors (34), and transducers (32). In one embodiment, the processing of the input signal from sensor (22) takes place in a waveform generator (24) comprising a phase-locked loop, a frequency divider, a shift register, and at least one switched capacitor filter. In another embodiment the input signal processing takes place in separate feedforward circuitry including a field programmable gate array (64).

20 Claims, 5 Drawing Sheets

ACTIVE NOISE AND VIBRATION CANCELLATION SYSTEM

FIELD OF THE INVENTION

This invention relates to the area of active control. Specifically, the invention relates to the area of active noise and vibration cancellation using adaptive feedforward filter systems.

BACKGROUND OF THE INVENTION

Vibration isolation and sound isolation systems are well known in the art. These systems utilize microprocessors to supply canceling waves to cancel or minimize vibration or sound within a defined area. The canceling waves are generally responsive to an external input signal(s). Examples of such systems are taught in U.S. Pat. Nos. 4,677,676 to Eriksson, 4,153,815 to Chaplin, 4,122,303 to Chaplin et al., 4,417,098 to Chaplin et al., 4,232,381 to Rennick et al., 4,562,589 to Warnaka et al., 4,473,906 to Warnaka et al., 4,878,188 to Zeigler, Jr., 5,170,433 to Elliott, 5,133,527 to Chen et al., and 4,689,821 to Salikudden et al., the disclosures of each which are hereby incorporated by reference herein. In these systems, the control scheme that is used can be least mean square (LMS), Filtered-X LMS, or the like.

Some active control systems utilize adaptive feedforward control. These systems operate on the input disturbance to generate a cancellation force. Such systems in the prior art utilize a Digital Signal Processor (DSP) as the CPU to implement the feedforward path, i.e., processing of the input signal and also for implementing the adaptation path, i.e., calculating the adaptation weight coefficients. Notably, because the same DSP is used to perform the calculations for the feedforward and adaptive paths simultaneously, the computational burden is immense in these prior art systems.

The feedforward path generally requires a high data flow rate because it is filtering the input waveform to produce output signal(s) or canceling waves to an output transducer (speaker or actuator). In general, the data flow rate must be many times higher than the highest frequency to be controlled. On the other hand, the adaptation path does not require the same high data flow rate. In fact, the adaptation path may be shut down temporarily whereas the feedforward path may never be. Therefore, there is a need for a system that will implement the feedforward path and the adaptation path, yet will economize on the DSP's computational load.

SUMMARY OF THE INVENTION

In light of the benefits and drawbacks of the prior art systems, the present invention provides an active noise or vibration control system which utilizes two separate hardware configurations to implement separately the feedforward and adaptation paths. This allows each configuration to be optimized for cost, size, and efficiency. In another aspect, the feedforward path is implemented in a waveform generator utilizing a phase-locked loop, two switched capacitor filters, a frequency divider, and a shift register. In the preferred embodiment, the feedforward path is implemented in a field programmable gate array (FPGA). This configuration is known as digital feedforward architecture with an adaptation update.

It is a key advantage of the present invention that when the feedforward implementation takes place on dedicated hardware outside the DSP, the DSP can be downsized. Significant cost savings are realized by eliminating the need to oversize the DSP capabilities to be able to manage the worst case computational loading, such as concurrent tonal interrupt.

It is an advantage of the present invention that it makes it possible to process tonal systems with large numbers of sensors and actuators with only one CPU, thus reducing cost, board area, power requirements and component count. Additional advantages of the digital feedforward architecture include increased logic density, throughput, reduced cost, improved adaptability and reliability.

The above-mentioned and further features and advantages of the present invention will become apparent from the accompanying descriptions of the preferred embodiments and attached drawings.

BRIEF DESCRIPTION OF THE DRAWINGS

The accompanying drawings which form a part of the specification, illustrate several embodiments of the present invention. The drawings and description together, sere to fully explain the invention. In the drawings.

DETAILED DESCRIPTION OF THE INVENTION

Figure 1:
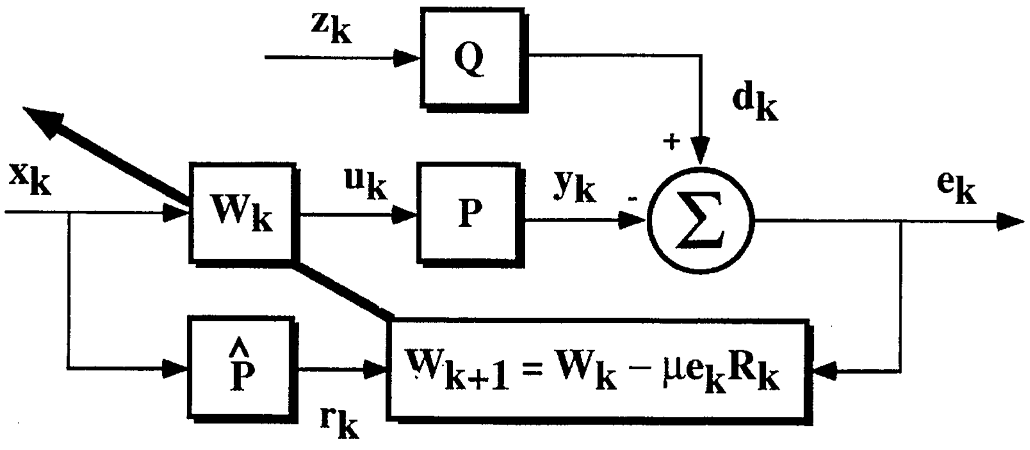
FIG. 1 is a block diagram illustrating a typical feedforward active control system.

The block diagram of FIG. 1 illustrates a general implementation of the adaptive least mean square (LMS) feedforward filter for active noise or vibration control. The embodiment of FIG. 1 applies to both tonal and broad band implementations. The $W_k$ block represents the feedforward path and the $W_{k+1}$ block represents the adaptation path. Where:

$W_k$=feedforward computations $W_k$+1=Adaptation computations $X_k$=input signal P=Plant $\hat{P}$=estimate of the error path $u_k$=control effort to produce $y_k$ $z_k$=actual disturbance Q=Plant from the disturbance to the location of interest $d_k$=disturbance at the location of interest $y_k$=canceling disturbance $e_k$=residual disturbance $r_k$=error path estimates $R_k$=matrix or $r_k$ values μ=adaptation coefficient.

An input signal $x_k$ is a signal indicative of the frequency content of the disturbance and is typically provided by a tachometer, accelerometer or the like. $\hat{P}$ is an estimation of the error path. By inputting $x_k$ into the estimate $\hat{P}$, an estimation of the filtered reference signal $r_k$ can be obtained (Filtered-X). $W_k$ represents the feedforward path. $u_k$ represents the control effort, i.e., the force that must be applied to the plant P in order to produce the cancellation pressure or vibration at the point of cancellation. $Z_k$ represents the actual disturbance, such as a rotary unbalance, etc. Q is the transfer function representing the plant from the disturbance source to the location of interest. The Q transfer function changes the disturbance into a noise or vibration that is experienced. $d_k$ is the disturbance with no control measured at the location of interest and $y_k$ is the cancellation force. The ideal force would be such that the error signal or residual $e_k$ is made zero. If this is not possible, then a minimal value is sought. $R_k$ is a matrix of delayed $r_k$ values. The number depends on the number of delay taps. The plant P is determined by on-line or off-line training. μ represents the adaptation coefficient. The present invention implements the adaptive least mean square (LMS) feedforward filter for active noise or vibration control in a novel way by allowing the signal generation to be conducted in separate hardware such that the digital signal processor is not burdened with this task and is dedicated to adaptation path processing.

Figure 2:
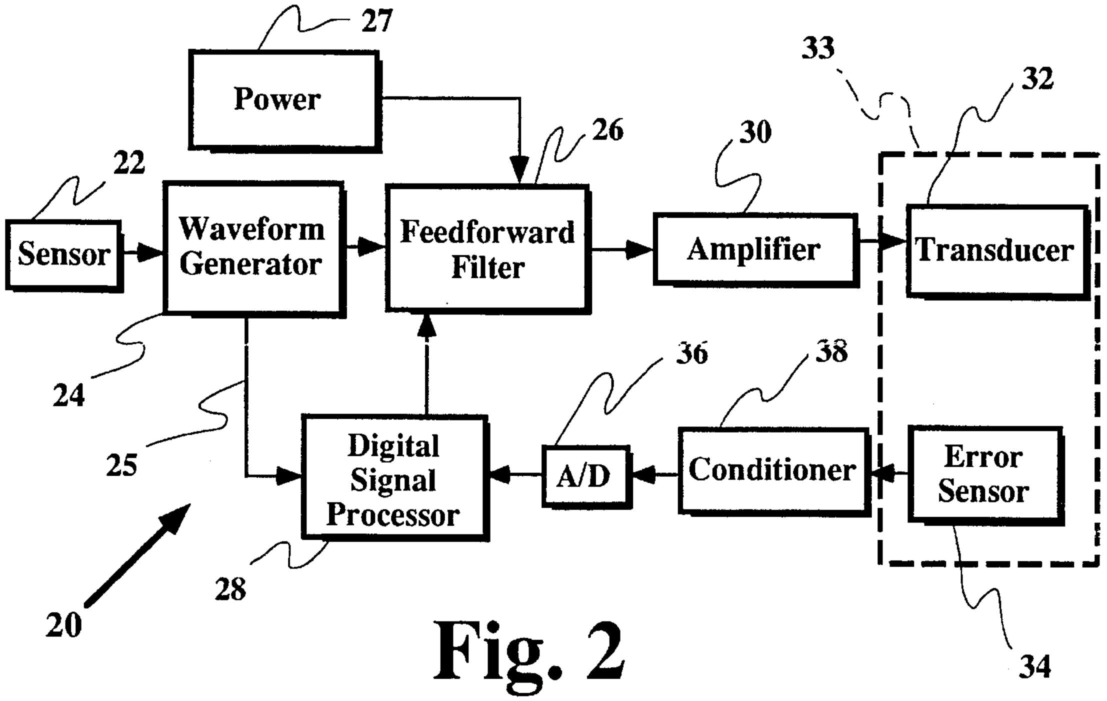
FIG. 2 is a block diagram illustrating the present invention active system utilizing a switched capacitor-type waveform generator for supplying analog signals to the feedforward filter.

FIG. 2 illustrates an embodiment of active control system 20 whereby the input signal processing is performed by a waveform generator 24 which is comprised of phase-locked loop, a frequency divider, a shift register, and multiple switched-capacitor filters. The active control system 20 is comprised of an input sensor 22 for providing a signal indicative of the disturbance source. One such signal could be from a tachometer. It should be understood that the appropriate filtering, amplifying or other conditioning would need to be performed on the sensor signal. The waveform generator 24 is fully described in co-pending application Ser. No. 08/245,719 filed contemporaneously herewith entitled "Waveform Generator", the disclosure of which is hereby incorporated by reference herein.

The feedforward circuitry 26 may include a feedforward filter having multiple adaptive weights whereby the adaptation weight coefficients are supplied by a DSP 28. Other central processing units (CPUs) could be utilized as well; DSPs are shown here merely as illustrative. The digital signal processor (DSP) 28 is used solely for calculating the coefficient weights. Line 25 can be implemented to feed a trigger signal to the DSP 28 to calculate the weights. Furthermore, line 25 may be used for providing timing or interrupt signals from the feedforward path to the adaptation path. In this embodiment, the waveform generator 24 forms a part of an interrupt circuit, interrupting the CPU at least four times a period to synchronize the output of the CPU to the feedforward path The sinusoidal signal which is output from the feedforward circuitry 26 is amplified by an amplifier 30 and fed to at least one transducer 32. The transducer 32 can be an actuator and/or a speaker. For example, the actuator may be an active mount, structural actuator, or inertial shaker or mass, or the like. The speaker may be a magnet driven standard speaker or a vibrating panel. The at least one error sensor 34 is used to supply information on the residual vibration or noise, i.e., the residual disturbance within the control volume 33 to the distal signal processor 28. A power source 27 provides power to the various components. An A/D converter 36 and signal conditioner 38 are usually required for each error sensor. Signal conditioner 38 may include a band pass filter or high pass filter, as necessary. The error sensor(s) 34 may be microphones, accelerometers, or the like. One significant advantage of providing separate hardware for the adaptation and feedforward paths is that control may then take place in a block mode fashion, i.e., round-robin control of each tone separately for a period of time then switching over to the next tone.

Figure 3:
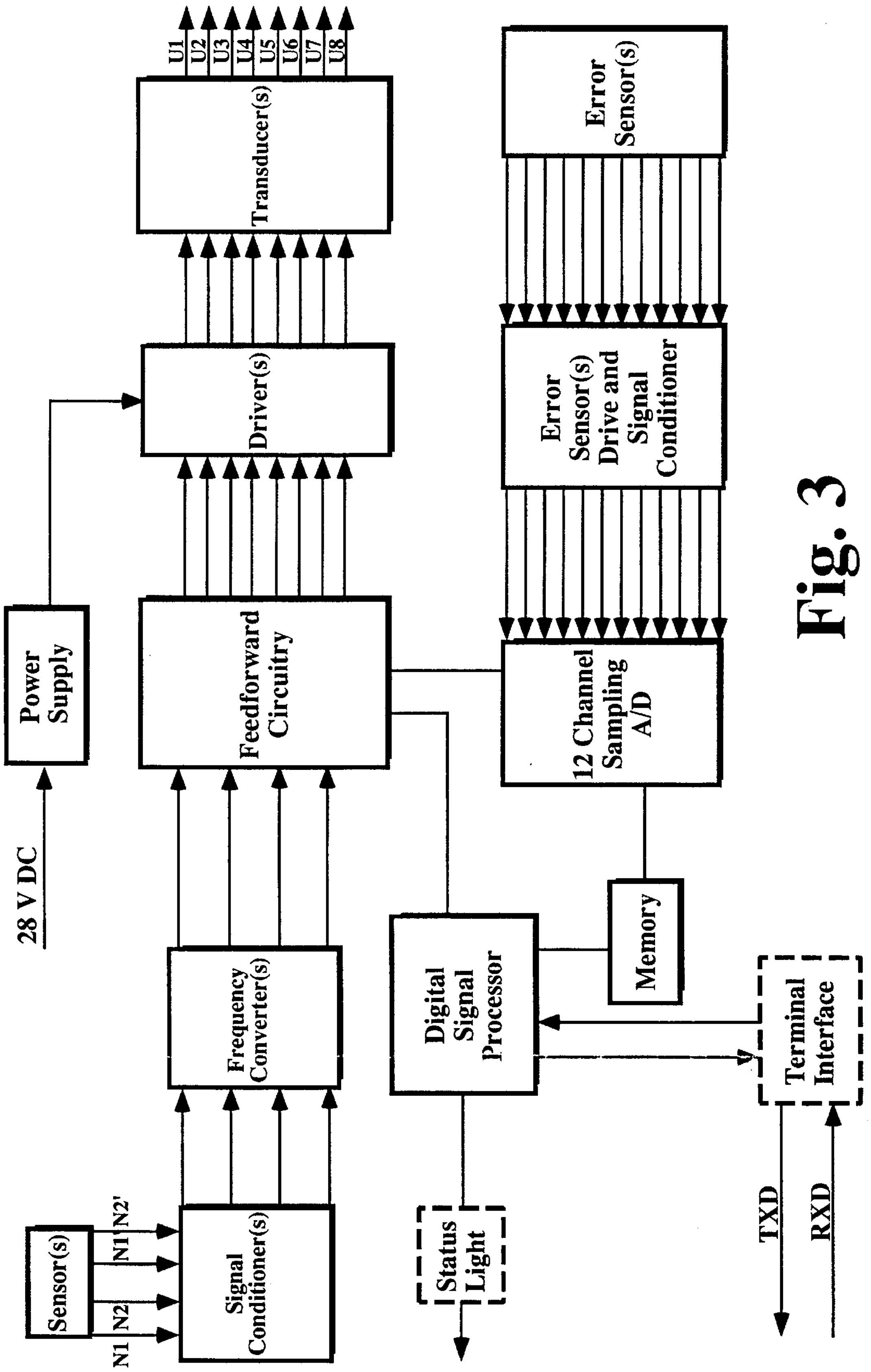
FIG. 3 is a block diagram illustrating the present invention utilizing separate feedforward circuitry for implementing the feedforward path and a dedicated DSP for the adaptation path.
Figure 4:
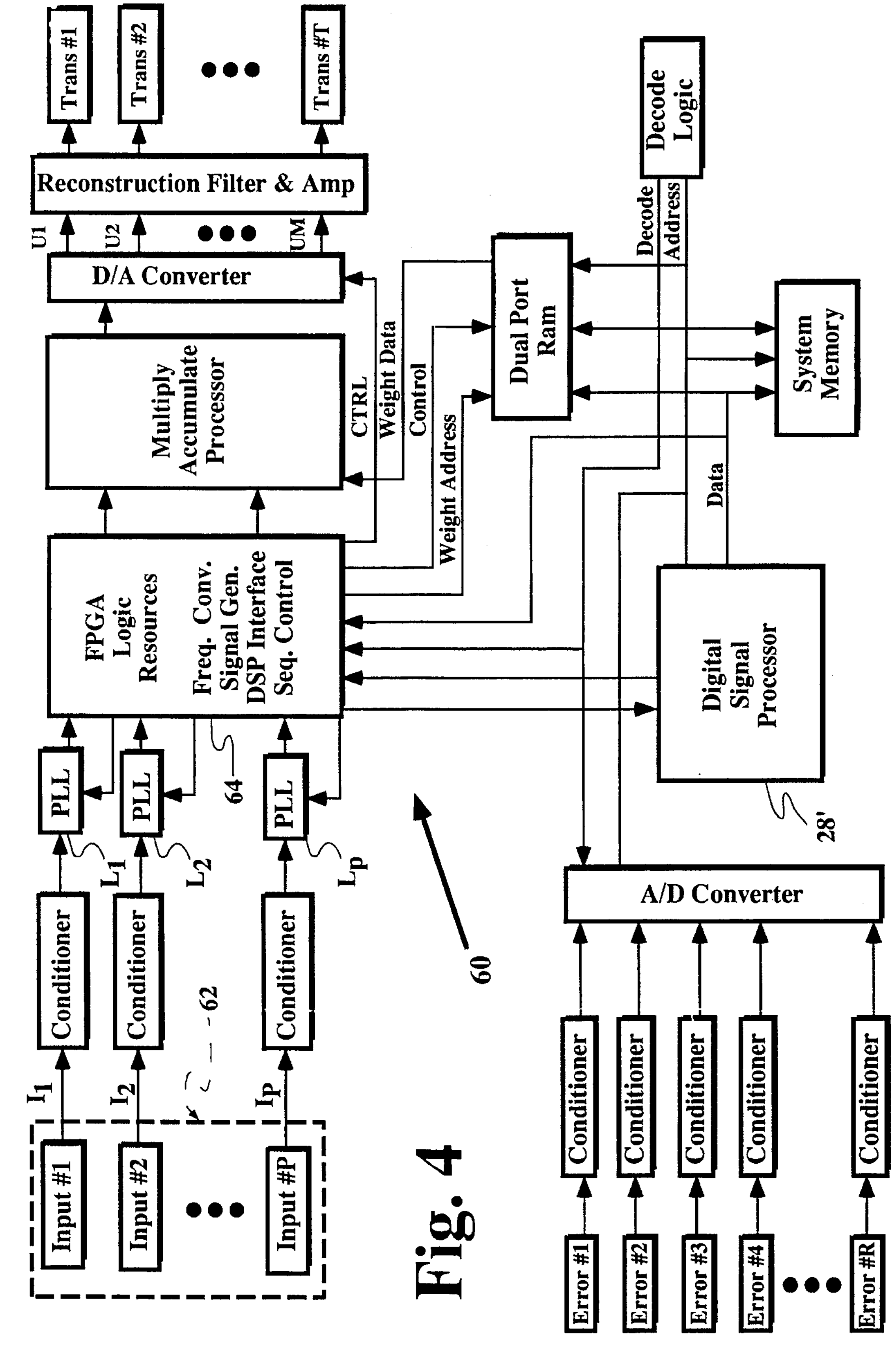
FIG. 4 is a block diagram illustrating a multiple input and output embodiment utilizing separate circuitry for separately implementing the feedforward and adaptation paths.

A second preferred embodiment is depicted in FIGS. 3 and 4 generally at 60. FIG. 3 depicts the data flow through the feedforward architecture and the actual hardware will be discussed in describing FIG. 4. As in the previous embodiment, separate hardware is provided to perform the computations for the feedforward path from that provided for the adaptation path. This particular configuration is known as digital feedforward architecture with an adaptation update and is preferred because of significant advantages in the realms of density, throughput, cost, adaptability, and reliability. The system will be described in conjunction with a configuration including four input tones, eight independent outputs and twelve error signals, although it will be appreciated that much larger arrays of input and output transducers can be accommodated by this hardware. The four tones input are the primary operational frequencies $N_1$ and $N_2$ of an aircraft's power plants and their first harmonics $N_1'$ and $N_2'$. The frequency range of operation is between 20 and 600 Hz.

At least one input tone I is received, with FIG. 4 indicating capability to process multiple inputs $I_1$ through $I_p$ (4 in our example). These inputs are derived from a sync signal input circuit 62 which provides a continuous stream of M pulses per cycle (shaft revolution), where M is a ratio of integers which may be from 1 to 2048 in the numerator to 1 to 2048 ($2^{\wedge 11}$) in the denominator. A frequency multiplier, in this case, phase-locked loops $L_1$–$L_p$, convert the input signals $I_1$–$I_p$ into an integer multiple, N, of the shaft frequency.

Since M can be a ratio of integers, it may be necessary for the loops $L_1$–$L_p$ to divide as well as multiply, the input signals, in some applications. This can be accommodated in the design of the particular phased-locked loops. In any event, the output frequency $f_1'$ will be N/M times the input frequency, $f_1$. The integer N is the over sampling rate of the digital sampling system. For this example, N is chosen as 16. N×NX transitions increment a modulo 16 counter within the field programmable gate array (FPGA) 64 which serves as a pointer into the sin/cos table. The FPGA chosen for this application was a 4000 series XILINX, although other logic resource systems could be used.

Figure 2A:
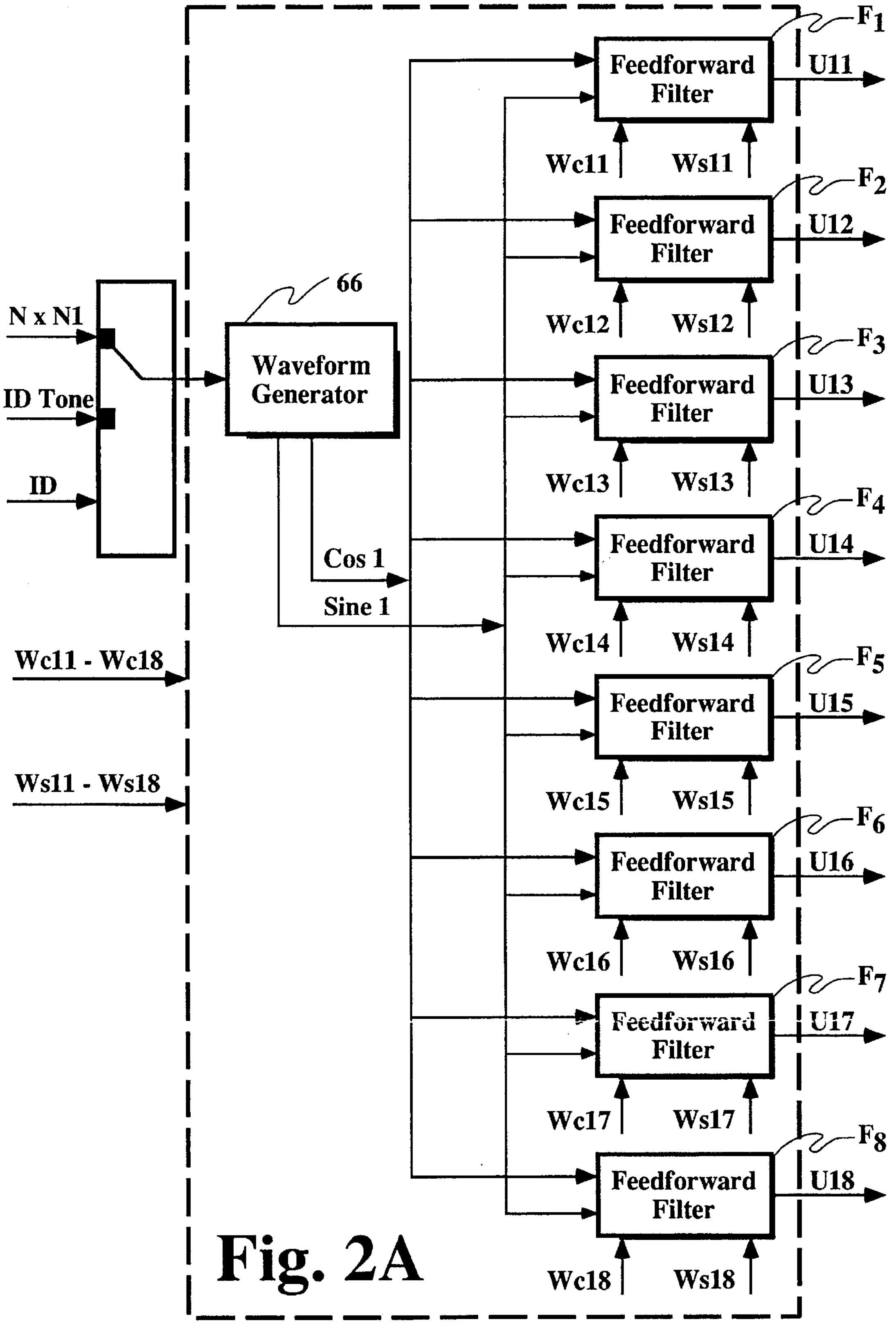
FIG. 2A is a block diagram illustrating the data flow through the feedforward system of a single input disturbance signal.

Each tone has its own pointer which successively steps through the sine table in increments of 2*pi/16 radians. Since each pointer is incremented by its respective input clock, each channel will generate digital sinusoidal signal pairs, namely a cosine wave and its quadrature sine wave, at its corresponding disturbance frequency, $f_1'$–$f_p'$. The modulo 16 counter and lookup table are identified in FIG. 2A as waveform generator 24'. Each of these pairs of waveforms is fed to one of a series of T feedforward filters $F_1$–$F_T$, with T being equal to the number of output signals, U. Each tone $N_{1-4}$ will produce T output components, represented as U(N,T).

The CPU, a DSP 28' having been chosen for this application, performs a number of functions. It will be understood that other CPUs could be utilized and, indeed, may be preferred for certain applications. The primary function of the DSP is to calculate the weighting factors $W_s$ and $W_c$ to be applied to each digital feedforward filter $F_1$–$F_T$ using a particular algorithm preferably a LMS adaptation algorithm, and most preferably, a Filter-X LMS algorithm. Since the feedforward calculations are performed on dedicated hardware, the DSP chip requirements are significantly reduced. The updating of filter weight sine and cosine values, can be performed at a much slower rate than is required for the computations being performed on the feedforward path. Accordingly, the demands placed upon the DSP are further reduced.

The sine and cosine filter weights $W_s$11–$W_s$18 and $W_c$11–$W_c$18 computed by the CPU are fed to digital feedforward filters $F_1$–$F_8$ (FIG. 2A) and used to multiply (provide amplitude weighting for) the pairs of sines and cosines which are representative of frequency and amplitude of the input signal to produce output filter components $U_{11}$–$U_{18}$. The formula used in the computation is generically, $W_c$(N, U)*(cos N)+$W_s$(N,U)*(sin N), where N is the number of the respective input disturbance signal and U is the number of the respective output signal.

Figure 2B:
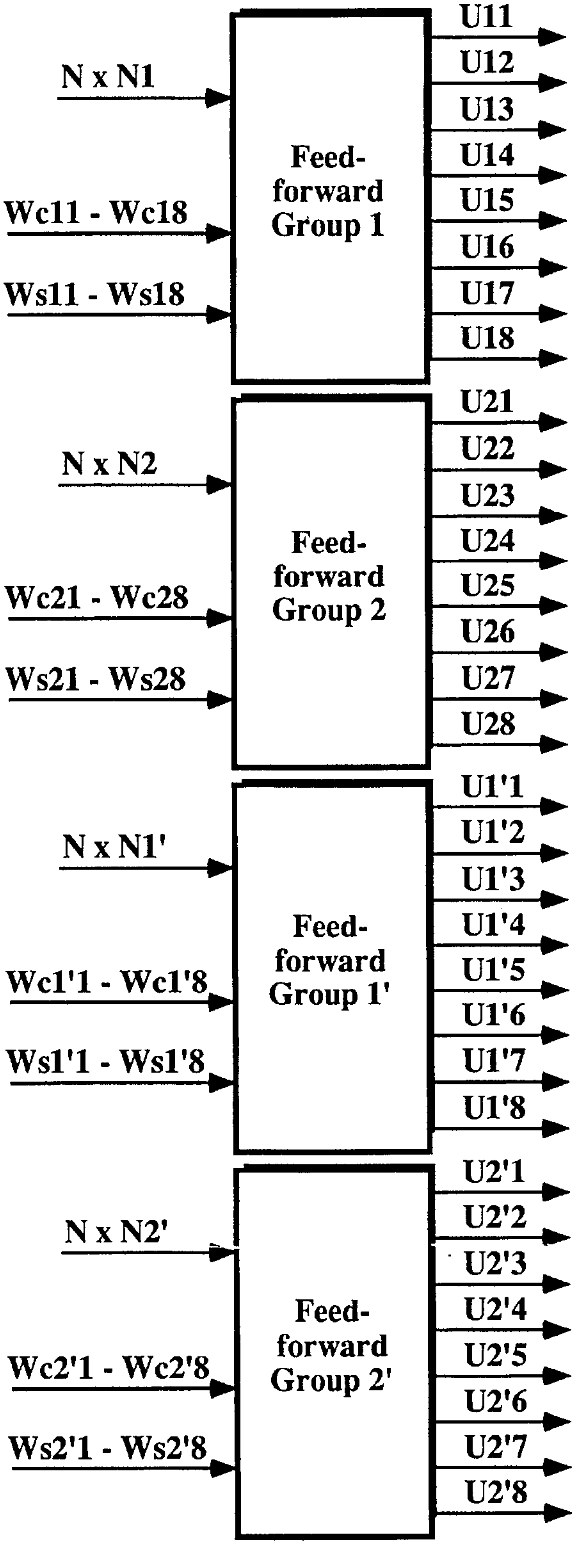
FIG. 2B is a block diagram illustrating four concurrent computational processes being carried out on the four input tones.
Figure 2C:
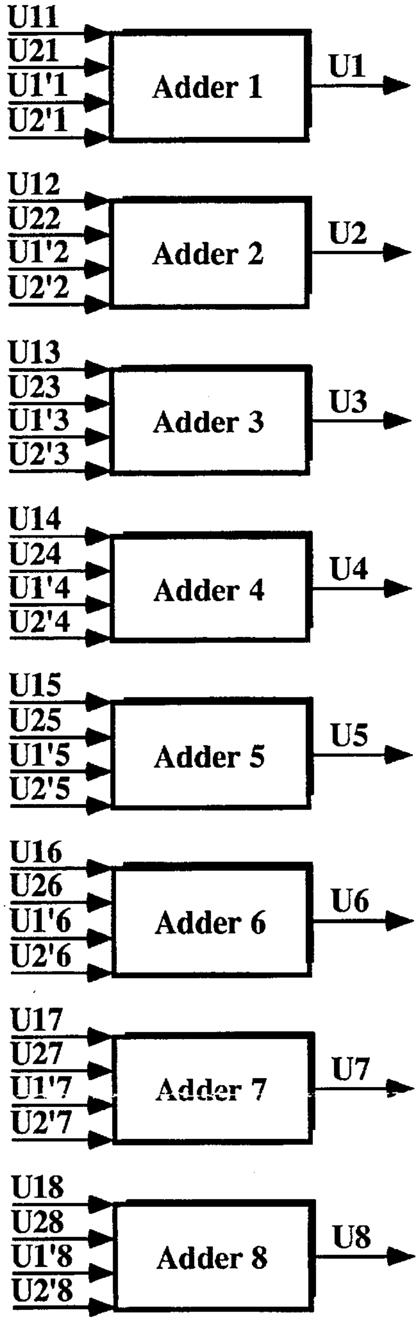
FIG. 2C is a block diagram illustrating the combination of signal components in the adder.

For the four input, eight output system depicted here, a total of 32 output component signals as shown in FIG. 2B are produced. It would be possible to process these 32 output components through independent processing paths. While this is feasible, although unwieldy for the 4×8 system depicted here, for larger arrays such processing becomes completely unworkable and slow. Within the FPGA 64, is a 4×4 to 1 multiplexer which combines four 4 bit components, one from each input tone, into a single output signal UT, as depicted in FIG. 2C. This reduces the number of processing paths by a factor equal to the number of input tones, greatly reducing the downstream logic resources needed to process these signals.

Two dual port rams (CY7C141) 70 form a 16 Bit data interface between the DSP 28' and the digital feedforward circuitry. The sequence controller within the FPGA 64 will control the address sequencing of the data output from the feedforward side of the rams and provide an interface to the DSP. Ram data accesses set up at the multiplier accumulate processor chip X register 72, and the data clocked into the register at the next XYCLK transition.

The arithmetic functions of the feedforward filter are implemented by a CY7C510 multiply/accumulate bit slice chip 72. Control output computations consist of a series of multiply and accumulate operations. A completed result is loaded into its corresponding digital-to-analog converter (DAC) 74 input register at the end of the cycle.

The FPGA 64 includes an ID multiplexer network which is a simple two to one mux which, under the control of the DSP, chooses between the $N_1$ synchronization input and a DSP generated input. At system initialization, the DSP will take control of the feedforward circuitry to determine the transfer functions between each control output and each error sensor in the system. This provides an initial best guess of the characterization of the system to permit signal processing to begin.

A number of error sensors, in this example 12, produce error signals $E_1$–$E_R$ where R equals 12. These error signals are conditioned (filtered and amplified as necessary) by conditioners 78 converted to digital signals by digital to analog converter 80 and fed into the DSP to adjust the filter weights to provide better cancellation than the original guesses implemented in the initialization of the system.

The digital to analog converter (MP7613) 74 supplies eight 12 bit DACs on a single chip. The microprocessor compatible interface consists of control lines plus eight 12 bit input registers which are double latched to allow simultaneous updates of the outputs. The digital sequence controller within the FPGA appropriately sequences the control to latch the control outputs into the DAC, as well as controlling the sequencing of most of the other operations in the circuit. This sequencing of functions includes interrupting the CPU at least four times per period to synchronize the output thereof to the feedforward circuit. The digital to analog converter 74 feeds a plurality of analog voltage signals to a like plurality of transducers, in our example, 8. These transducers may take the form of one of a group including an active component of a speaker, a transducer directly attached to an aircraft structural component, and an actuator within an active mount. In each instance, the output cancellation signals will minimize the impact of the input disturbance signal upon the aircraft.

In operation, the DSP will compute out updated filter weights (amplitude values) using the Filtered-X algorithm and input from the error sensors and feed them to the feedforward signal processor. The feedforward circuitry will calculate the frequency and phase of the output signals needed and form a product of the filter weights and sine/cosine signals which minimize the effects of the input disturbance. A sync signal is used because it is desirable that the input not be amplitude sensitive. The output is then transformed by a digital-to-analog converter into a signal that the transducers can recognize. The use of separate hardware to perform the digital feedforward and adaptation path calculations permits the size of the CPU to be optimized and the faster feedforward data need not be slowed down by the processing of the slower adaptation calculations.

While several embodiments of the present invention have been described in detail, various modifications, alterations, changes and adaptations to the aforementioned may be made without departing from the spirit and scope of the present invention defined in the appended claims. It is intended that all such modifications, alterations, changes and adaptations be considered part of the present invention.

What is claimed is:

1. A digital processor for processing at least one tonal input disturbance signal to produce one or more counter-phased frequency cancellation output signals to minimize the effects of said disturbance signal(s), said processor including separate adaptation and feedforward paths and comprising:

(a) a sync signal input circuit for providing a signal related to a frequency, $f$, of said at least one input disturbance signal to be minimized, said circuit producing M input pulses per cycle where M is a ratio of integers;

(b) a frequency multiplier which converts said M pulses per cycle into an integer multiple, N, of said frequency $f$;

(c) a sine/cosine waveform generator for providing a pair of signals, each pair including a cosine signal and its quadrature sine signal representative of said frequency and phase of said at least one disturbance signal for each of said N multiples thereof;

(d) a plurality of T feedforward filters each receiving a pair of signals from said waveform generator and multiplying said pair of signals by a particular weighting factor said plurality T being equal to the number of output signals;

(e) a central processing unit (CPU) for computing said particular weighting factors of said adaptation path;

(f) an arithmetic processing unit for multiplying said weighting factors times said sine and cosine signals and adding said signals according to a predetermined formula to produce one or more digital output signals;

(g) an analog-to-digital converter which receives one or more error signals as an analog voltage and converts said signal(s) to digital form, said error signal(s) being utilized to alter the weighting factors calculated by said CPU;

(h) a sequence controller for carrying out a repetitive sequence of calculations within the feedforward path;

(i) a CPU data interface permitting calculated data to be transmitted to and from said CPU of said adaptation path from and to various components of said feedforward path;

(j) a CPU synchronization network including an interrupt circuit to interrupt said CPU at least four times per period to synchronize the output of said CPU to said feedforward path;

(k) a digital-to-analog converter to transform said one or more digital output signals from said arithmetic processing unit to analog form; and (l) means responsive to said one or more analog output signals to minimize said input disturbance signal(s).

2. The digital processor of claim 1 wherein said arithmetic processing unit comprises a bit slice processor.

3. The digital processor of claim 2 wherein said predetermined formula comprises $W_c(N,U)*\cos N+W_s(N,U)*\sin N$, where $W_c$ and $W_s$ are, respectively, the cosine and sine weighting factors computed by said DSP, N is the number of the respective input disturbance signal and U is the number of the respective output signal.

4. A digital processor of claim 1 wherein a field programmable gate array (FPGA) provides a group of logic resources for performing such functions as frequency conversion, signal generation, CPU interface and sequential control.

5. The digital processor of claim 4 wherein said CPU data interface comprises an address toggle within said FPGA and two random access memory chips for storing computed weight data.

6. The digital processor of claim 1 further comprising means for enabling simultaneous processing of plural input disturbance signals.

7. The digital processor of claim 6 wherein said means for enabling simultaneous processing of plural input disturbance signals comprises multiple phase-locked loops which each process an input signal, and a multiplexer to combine portions of each input into a single multibit signal to reduce said signal paths by a factor equal to the number of input signals.

8. A digital processor of claim 1 wherein said CPU comprises a digital signal processor.

9. A digital processor of claim 1 wherein said output signals are fed to one of a group including a sneaker, a transducer attached to a aircraft structural component, and an actuator within an active mount.

10. An active control system, comprising:

(a) a digital signal processor for calculating weights in an adaptation path; providing an output control signal to a feedforward circuit and (b) a separate waveform generator for i) implementing a feedforward path by supplying sinusoidal control signal outputs to said feedforward circuit, said feedforward circuit which separately processes an input signal to arrive at particular phases and frequencies of said sinusoidal control signal to produce an active vibration control signal, and ii) supplying timing signals to said digital signal processor which are synchronized to said input signal from an input source;

whereby the digital signal processor is freed from having to manipulate any data associated with the feedforward path.

11. An active system of claim 10 wherein said waveform generator further includes:

(a) a phase-locked loop having a first phase-locked loop input for receiving an input signal from a source, a second phase-locked loop input, and a phase-locked loop output for outputting a multiplied square wave signal whose frequency is a multiple of said input signal frequency;

(b) a frequency divider having a frequency divider input for receiving said multiplied square wave signal from said phase-locked loop, a frequency divided output including at least one divided output signal, one of said at least one divided output signal being received by said second phase-locked loop input of said phase-locked loop; and (c) a first switched capacitor filter having a first clock input for receiving said multiplied square wave signal from said phase-locked loop, a first switched capacitor filter input on said first switched capacitor filter for also receiving one of said at least one divided output signal, and a switched capacitor filter output for outputting a first analog wave which is synchronized to said input signal.

12. An active system of claim 10 wherein said waveform generator further includes:

(a) a phase-locked loop having a first phase-locked loop input for receiving an input signal from said source, a second phase-locked loop input, and a phase-locked loop output adapted for outputting a multiplied square wave signal;

(b) a frequency divider having a frequency divider input for receiving said multiplied square wave signal from said phase-locked loop, said frequency divider outputting a frequency divider output which includes at least one divided output signal, one of said divided output signal being received by said second phase-locked loop input of said phase-locked loop;

(c) a first switched capacitor filter having a first clock input for receiving said multiplied square wave signal from said phase-locked loop, a first switched capacitor filter input for also receiving one of said at least one divided output signal from said frequency divider, and a first switched capacitor filter output for outputting a first analog wave which is phase synchronized to said input signal from said source;

(d) a second switched capacitor filter having a second clock input for receiving said multiplied square wave signal from said phase-locked loop, a second switched capacitor filter input, and a second switched capacitor filter output for outputting a second analog wave which is phase shifted from said first analog wave; and (e) a shift register having an a third clock input for receiving said multiplied square wave signal from said phase-locked loop, a shift register input for also receiving one of said at least one divided output signal from said frequency divider, and a shift register output for outputting a phase shifted signal which is received in said second switched capacitor filter input.

13. An active system of claim 10 wherein said waveform generator also provides a 4× signal for use by said digital signal processor to trigger said digital signal processor to calculate LMS adaptation coefficients.

14. An active system of claim 10 wherein said frequency divided output also provides one of a multiple and submultiple signal for use as a synchronizing input to a second waveform generator for controlling a second harmonic of said input source.

15. An active system of claim 10 wherein said frequency divided output also provides a 1× signal and a 2× signal for use by said digital signal processor to determine the phase of said first analog wave and said second analog wave.

16. A process of cancelling one of a mechanical vibration and noise, comprising the steps of:

(a) inputting said input signal into a first phase-locked loop input of a phase-locked loop;

(b) outputting a multiplied square wave signal to an input of a frequency divider, to a first clock input of a first switched capacitor filter, to a second clock input of a second switched capacitor filter, and to a third clock input of a shift register;

(c) dividing said multiplied square wave signal in said frequency divider thereby providing a frequency divided output including at least one divided output signal and sending one of said at least one divided output signal to a second phase-locked loop input of said phased lock loop, to a shift register input of said shift register, to a first switched capacitor filter input of said first switched capacitor filter, and to a digital signal processor;

(d) receiving a shifted signal from said shift register into a second switched capacitor filter input of said second switched capacitor filter;

(e) outputting a first analog wave from said first switched capacitor filter and a second analog wave from said second switched capacitor filter, said first analog wave being synchronized with said input signal and said second analog wave being phase shifted from said first analog wave;

(f) receiving said first and said second analog waves at a feedforward circuit;

(g) receiving at least one divided output from said frequency divider as a timing signal in said digital signal processor; and (h) calculating the weights for an adaptation path in said digital signal processor and supplying said weights to said feedforward circuit to supply a cancelling signal to a transducer.

17. A waveform generator of claim 16 wherein said first wave is a cosine wave and said second wave is a phase shifted wave and are both input into a feedforward filter controlled according to an LMS algorithm.

18. A controller for a system which actively cancels vibrations by providing cancellation signals that are out-of-phase sine waves of appropriate frequency and magnitude from a plurality of transducers, said controller comprising:

a) a digital signal processor (DSP) for calculating weights in an adaptation path determining a magnitude of cancellation signal needed;

b) a separate feedforward signal processor for implementing a feedforward path by i) digitally calculating a frequency and phase of control signals needed for a feedforward circuit, ii) for supplying timing signals to said digital signal processor which are synchronized to an input source, and iii) digitally multiplying said weights calculated by said DSP by said control signal;

c) a digital-to-analog converter to change said digital control signals into analog outputs which can be fed to said plurality of transducers;

whereby all of said computations by said DSP and said feedforward processor are performed digitally.

19. The controller of claim 18 wherein said feedforward processor comprises a field programmable gate array (FPGA) and a digital multiply accumulate resource.

20. The controller of claim 19 wherein said FPGA provides a group of logic resources for performing functions including frequency conversion, signal generation, DSP interface and sequential control.

* * * * *